(12) United States Patent
Ditzel et al.

(10) Patent No.: US 9,505,703 B2
(45) Date of Patent: Nov. 29, 2016

(54) CARBONYLATION PROCESS

(71) Applicant: BP Chemicals Limited, Middlesex (GB)

(72) Inventors: Evert Jan Ditzel, East Yorkshire (GB); Bogdan Costin Gagea, Berkshire (GB); Nicholas John Hazel, East Yorkshire (GB); John Glenn Sunley, East Yorkshire (GB); Gordon John Haining, East Yorkshire (GB)

(73) Assignee: BP CHEMICALS LIMITED, Middlesex (GB)

( * ) Notice: Subject to any disclaimer, the term of this patent is extended or adjusted under 35 U.S.C. 154(b) by 0 days.

(21) Appl. No.: 14/773,034

(22) PCT Filed: Mar. 6, 2014

(86) PCT No.: PCT/EP2014/054392
§ 371 (c)(1),
(2) Date: Sep. 4, 2015

(87) PCT Pub. No.: WO2014/135660
PCT Pub. Date: Sep. 12, 2014

(65) Prior Publication Data
US 2016/0052857 A1    Feb. 25, 2016

(30) Foreign Application Priority Data
Mar. 8, 2013  (EP) .................... 13158468

(51) Int. Cl.
| | | |
|---|---|---|
| *C07C 67/36* | (2006.01) | |
| *C07C 67/37* | (2006.01) | |
| *B01J 29/18* | (2006.01) | |
| *B01J 29/50* | (2006.01) | |
| *B01J 29/65* | (2006.01) | |
| *B01J 29/70* | (2006.01) | |
| *C07C 51/09* | (2006.01) | |

(52) U.S. Cl.
CPC ............. *C07C 67/37* (2013.01); *B01J 29/18* (2013.01); *B01J 29/50* (2013.01); *B01J 29/65* (2013.01); *B01J 29/7015* (2013.01); *B01J 29/7026* (2013.01); *C07C 51/09* (2013.01)

(58) Field of Classification Search
CPC ....... C07C 67/37; C07C 69/14; C07C 51/09; B01J 29/18; B01J 29/50; B01J 29/65; B01J 29/7015; B01J 29/7026
See application file for complete search history.

(56) References Cited

U.S. PATENT DOCUMENTS

2011/0319654 A1 * 12/2011 Hazel .................... C07C 67/37
560/232

FOREIGN PATENT DOCUMENTS

| EP | 1 985 606 A1 | 10/2008 |
|---|---|---|
| EP | 1985606 | * 10/2008 |
| WO | WO2008132438 | * 11/2008 |
| WO | WO 2010/058149 A1 | 5/2010 |
| WO | WO2010058149 | * 5/2010 |

OTHER PUBLICATIONS

Simoncic et al. (Peculiarity and defect structure of the natural synthetic zeolite mordenite: A single-crystal X-Ray study, American Mineralogist, vol. 89, pp. 421-431, 2004).*

* cited by examiner

*Primary Examiner* — Yevegeny Valenrod
*Assistant Examiner* — Blaine G Doletski
(74) *Attorney, Agent, or Firm* — Nixon & Vanderhye P.C.

(57) ABSTRACT

Process for the production of methyl acetate by carbonylating dimethyl ether with carbon monoxide in the presence of hydrogen and a zeolite catalyst. The process is carried out with a molar ratio of hydrogen to carbon monoxide of at least 1 and the catalyst has been calcined at a temperature of from about 375° C. to about 475° C.

29 Claims, 3 Drawing Sheets

CARBONYLATION PROCESS

This application is the U.S. national phase of International Application No. PCT/EP2014/054392 filed Mar. 6, 2014 which designated the U.S. and claims priority to European Patent Application No. 13158468.2 filed Mar. 8, 2013, the entire contents of each of which are hereby incorporated by reference.

This invention relates to a process for the production of methyl acetate by the carbonylation of dimethyl ether with carbon monoxide in the presence of hydrogen and a zeolite catalyst calcined at low temperature.

BACKGROUND OF THE INVENTION

Zeolites, and in particular mordenites, are used as catalysts in chemical processes, such as in carbonylation reactions of ethers and alcohols. For example EP 1985606 describes the production of methyl acetate by carbonylating dimethyl ether with carbon monoxide in the presence of zeolite catalysts, such as mordenites, at temperatures of greater than 250° C. to 350° C. and at pressures of at least 10 barg.

Mordenites are crystalline natural or synthetic zeolites of the aluminosilicate type. The mordenite structure is defined in the *Atlas of Zeolite Framework Types* (C. Baerlocher, W. M. Meier, D. H. Olson, 5$^{th}$ Ed. Elsevier, Amsterdam, 2001). Generally mordenites have a composition expressed in moles of oxide of $1.0 \pm 0.2 Na_2O, Al_2O_3, 10 \pm 0.5 SiO_2$ Instead of sodium other alkali or alkaline earth metals may also be present.

In general, the sodium form of mordenite is not particularly effective for the carbonylation of ethers and it has been found that replacing some or all of the sodium cations by hydrogen ions yields the more effective hydrogen form mordenite. Conversion of the sodium form to the hydrogen form can be accomplished by a number of means. One method is the direct replacement of sodium ions with hydrogen ions using an acidified aqueous solution where the process of ion-exchange is employed. Another method involves replacement of the sodium ions by ion-exchange with ammonium ions followed by decomposition of the ammonium form using a calcination method.

Catalysts for the carbonylation of ethers and alcohols can be prepared by combining commercially available hydrogen form mordenites with suitable binder materials, as described for example WO 2010/058149.

WO 2010/058149 describes a process for the preparation of methyl acetate and/or acetic acid by carbonylating dimethyl ether and/or methanol with carbon monoxide in the presence of a catalyst which catalyst is a H-mordenite bound with a mesoporous binder selected from silicas, aluminas, silica-aluminas, magnesium silicates and magnesium aluminium silicates.

An important aspect of any catalytic process is the performance of a catalyst when exposed to the desired process conditions. The improvement of catalytic performance in carbonylation reactions is a continuous objective of process and catalyst development research.

Mixtures of carbon monoxide and hydrogen (generally referred to as synthesis gas). are produced commercially and are readily available. Thus, it is desirable to conduct carbonylation processes using such synthesis gas mixtures. Typically, however, the synthesis gas mixtures are hydrogen-rich, that is hydrogen is present in such mixtures in at least an equimolar ratio and generally in an excess molar ratio to carbon monoxide. However, a hydrogen-rich feed means less space for carbon monoxide in the carbonylation reactor resulting in a reduced partial pressure of carbon monoxide and consequently a reduced rate of reaction. Thus, one problem which exists in carbonylation processes is that conducting the process under hydrogen-rich conditions increases the performance requirements of the catalyst.

SUMMARY OF THE INVENTION

Thus, it would be desirable if the catalytic properties of zeolite catalysts for use in carbonylation processes could be improved, and in particular for use in carbonylation processes conducted under hydrogen-rich conditions.

Applicant has now found that by calcining zeolite catalysts at low temperatures it is possible to achieve enhanced catalytic performance, such as enhanced activities and/or selectivities, in carbonylation processes of dimethyl ether with carbon monoxide carried out in the presence of an equimolar or molar excess of hydrogen.

Accordingly, the present invention provides a process for the production of methyl acetate which comprises carbonylating dimethyl ether with carbon monoxide in the presence of hydrogen and a zeolite catalyst wherein the process is carried out with a molar ratio of hydrogen to carbon monoxide of at least 1 and the catalyst has been calcined at a temperature of from about 375° C. to about 475° C.

The present invention further provides a process for improving the performance of a zeolite catalyst in the production of methyl acetate by the carbonylation of dimethyl ether with carbon monoxide in the presence of hydrogen wherein the process is carried out with a molar ratio of hydrogen to carbon monoxide of at least 1 and the catalyst has been calcined at a temperature of from about 375° C. to about 475° C.

In an embodiment of the present invention, the catalyst is calcined at a temperature of from about 400° C. to about 475° C., for example of from about 400° C. to about 450° C.

For the avoidance of doubt, the phrase 'a molar ratio of hydrogen to carbon monoxide of at least 1' means that the molar ratio of hydrogen/carbon monoxide is at least 1.

DETAILED DESCRIPTION OF THE INVENTION

A zeolite catalyst is employed in the present invention. Zeolites are crystalline aluminosilicates which have framework structures constructed from tetrahedra of SiO$_4$ and AlO₄ that share vertices. Each framework topology contains a regular array of pores, channels and/or pockets that vary in size, shape and dimensionality. These framework topologies or structure types of zeolites are assigned three-letter structure codes by the Structure Commission of the International Zeolite Association, under the authority of IUPAC. A description of zeolites, their structure, properties and methods of synthesis can be found in The *Atlas of Zeolite Framework Types* (C. Baerlocher, W. M. Meier, D. H. Olson, 5$^{th}$ Ed. Elsevier, Amsterdam, 2001) in conjunction with the web-based version (http://www.iza-structure.org/databases/).

Suitably, for use in the present invention, a zeolite contains at least one channel or pocket which is defined by an 8-member ring. Preferably, the 8-member ring channel or pocket is interconnected with at least one channel defined by a ring with 10 or 12 members. The window size of the zeolite channel systems should be such that the reactant dimethyl ether and carbon monoxide molecules can diffuse freely in and out of the zeolite framework. Suitably, the window size of an 8-member ring channel or pocket is at least 2.5×3.6 Angstroms.

In an embodiment of the present invention, the zeolite is selected from zeolites of framework type MOR, FER, OFF, CHA, GME and MFS.

Examples of zeolites of framework type MOR include mordenite. Examples of zeolites of framework type FER include ferrierite and ZSM-35. Examples of zeolites of framework type OFF include offretite. Examples of zeolites of framework type CHA include chabazite. Examples of zeolites of framework type GME include gmelinite.

Examples of zeolites of framework type MFS include ZSM-57.

In an embodiment, the zeolite for use in the present invention is selected from mordenite, ferrierite and offretite, preferably mordenite.

The zeolite is preferably associated with hydrogen, that is, a hydrogen-exchanged zeolite. Examples of hydrogen-exchanged zeolites useful in this invention include the hydrogen-exchanged form of zeolites of framework types selected from MOR, FER, OFF CHA, GME and MFS.

In an embodiment, the zeolite for use in the present invention is a hydrogen-exchanged zeolite of framework type MOR.

Other exchanged forms of zeolites which may be used in the present invention include ammonium exchanged zeolites. Examples of ammonium-exchanged zeolites useful in this invention include the hydrogen-exchanged form of zeolites of framework types selected from MOR, FER, OFF CHA, GME and MFS.

In an embodiment, the zeolite for use in the present invention is an ammonium-exchanged zeolite of framework type MOR.

In one embodiment of the present invention, the zeolite is mordenite, for example mordenite in a hydrogen-exchanged or an ammonium-exchanged form.

The silica to alumina molar ratio of the zeolite is the bulk or overall ratio. This can be determined by any one of a number of chemical analysis techniques. Such techniques include x-ray fluorescence, atomic absorption and ICP (inductive coupled plasma). All will provide substantially the same silica to alumina molar ratio value. The bulk silica to alumina molar ratio of the zeolite is suitably at least 5, and preferably less than or equal to 100, such as in the range of from 20 to 60, for example in the range of from 20 to 40.

The zeolite for use in the present invention may be employed in powder form or can optionally be employed in combination with a binder material (binder). The binder is preferably a refractory inorganic oxide for example an alumina, silica-alumina or a silica. A preferred binder is an alumina. Suitable aluminas include various hydrous aluminium oxides or alumina gels such as alpha-alumina monohydrate of the boehemite structure, alpha-alumina trihydrate of the gibbsite structure, beta-aluminas and gamma-aluminas. Alpha-aluminas of the boehemite type are preferred.

Other examples of suitable binders include titania, zirconias, magnesias and clay binders, such as bentonite and kieselguhr.

In an embodiment of the present invention the catalyst is mordenite, preferably a hydrogen-exchanged or ammonium-exchanged mordenite bound with a binder, for example a binder selected from aluminas, silica-aluminas and silicas, preferably aluminas.

The relative proportion of binder to zeolite may vary widely but is suitably from about 10% to 90% by weight, such as in the range 10% to 65%, preferably in the range 10% to 30% by weight.

A bound zeolite can be utilised in any suitable shape, such as in the form of an extrudate, pellets or beads, preferably in the form of an extrudate.

Processes for forming catalysts into shaped particles are well-known in the art and may be accomplished by forming a gel or paste of a zeolite powder with the addition of a binder material and extruding the gel or paste into the desired shape prior to drying.

In general, a process for preparing a catalyst suitable for use in the present invention, such as a catalyst which is an alumina-bound mordenite, comprises the steps of a) contacting a zeolite powder with binder in the presence of water and optionally a peptizing agent to form a mixture; (b) shaping the mixture to form a bound zeolite catalyst and (c) drying the catalyst.

More specifically, for example in step (a) a mordenite powder, alumina powder, water and optionally an acidic peptizing agent, such as nitric acid, may be mixed for a period necessary to obtain a wet homogeneous paste or slurry. Suitably, water and optional peptizing agent are present in step (a) in the range 30% to 70% of the mixture. The shaping in step (b) may comprise pressing, extruding or granulating to produce pellets, extrudates or beads. The drying in step (c) may be carried out at a temperature of from about 80° C. to about 120° C. The drying may be conducted for several hours to remove any excess peptizing agent, water and all or substantially all of the physisorbed water. Drying may be carried out either at atmospheric pressure or under reduced pressure.

Alternatively, a catalyst may be formed from a zeolite and binder by dry mixing of the zeolite and binder components. Dry mixing may be performed by intimately mixing a zeolite powder with dry binder to form a bound zeolite. The dry mixing may be carried out by any suitable mechanism, such as by tumbling or rotation. Dry mixing is suitable for the preparation of catalysts comprising mordenites and inorganic oxides such as aluminas, silica-aluminas and silicas.

Zeolite powders may also be formed into particles without the use of a binder.

The catalyst for use in the present invention is subjected to a low temperature calcination. Typically, zeolite catalysts, prior to use in carbonylation processes, are calcined at high temperature, such as at temperatures exceeding 500° C. However, advantageously, applicant has found that improved catalytic performance is achieved in carbonylation processes which are conducted in the presence of an equimolar or molar excess of hydrogen if the catalyst has been calcined at a temperature of from about 375° C. to about 475° C.

In an embodiment of the present invention, the catalyst is calcined at a temperature of from about 375° C. to about 450° C., for example of from about 400° C. to about 450° C.

In a further embodiment of the present invention, the catalyst is a mordenite in a hydrogen-exchanged or an ammonium-exchanged form bound with a binder selected from aluminas, silica-aluminas and silicas, preferably an alumina, which has been calcined at a temperature of from about 400° C. to about 450° C.

The catalyst may be calcined in the presence of an inert atmosphere, such as nitrogen, or in an oxidizing atmosphere such as oxygen or air. Preferably, calcining of the catalyst is carried out in air, for example in static air or flowing air.

In an embodiment of the present invention, the catalyst is a mordenite, such as a bound mordenite which has been calcined in air, for example in static air.

The duration of the calcination may be from about 10 minutes to about 10 hours, such as from about 20 minutes to about 5 hours, for example from about 20 minutes to about 3 hours, for instance from about 1 hour to about 3 hours.

To prevent or minimize local overheating of the catalyst, calcination is suitably controlled such that the temperature is increased in a controlled manner to the final calcination temperature. Controlled calcining may be effected by applying slow ramp rates to the desired calcination temperature. Suitably, the catalyst may be calcined at one or more ramp rates of from about 1° C./min to about 10° C./min., such as at one or more ramp rates of from about 1° C./min to about 5° C./min to the desired calcination temperature.

A suitable calcining procedure is to heat the catalyst, suitably in air, for example in static air, to a temperature of about 90° C. at a ramp rate of about 3° C./min, increase the temperature from about 90° C. to about 110° C. at a ramp rate of about 1° C./min and thereafter increasing the temperature from about 110° C. to the desired calcination temperature at a ramp rate of about 5° C./min.

Overheating of the catalyst during calcination may be further minimized by employing intermediate stops in the temperature ramp, for example stops having a duration of a few hours, such as stops of about 1 to about 3 hours. Suitably, calcining of the catalyst may be carried out by heating a catalyst, for example in air, to a temperature of about 90° C. at a ramp rate of about 3° C./min, holding at that temperature for about 2 hours, increasing the temperature from about 90° C. to about 110° C. at a ramp rate of about 1° C./min, holding at that temperature for about 2 hours and thereafter increasing the temperature from about 110° C. to the desired calcination temperature at a ramp rate of about 5° C./min.

In an embodiment of the present invention, the catalyst is calcined in air, for example in static air, at a temperature of from about 400° C. to about 475° C., for example of from about 400° C. to about 450° C. for a duration of from about 10 minutes to about 10 hours, such as from about 20 minutes to about 5 hours, for example from about 20 minutes to about 3 hours, for instance from about 1 hour to 3 hours.

The low temperature calcined catalysts are useful for the carbonylation of dimethyl ether with carbon monoxide to produce methyl acetate, and in particular in those carbonylation processes which are conducted in the presence of hydrogen.

The dimethyl ether may be substantially pure dimethyl ether. In commercial practice, dimethyl ether is produced by the catalytic conversion of synthesis gas (mixtures of hydrogen and carbon monoxide) over methanol synthesis and methanol dehydration catalysts. This catalytic conversion results in a product which is predominantly dimethyl ether but it may also contain some methanol. For use in the present invention, the dimethyl ether may comprise small amounts of methanol provided that the amount of methanol is not so great as to inhibit the production of methyl acetate reaction product. Suitably, the dimethyl ether for use in the present invention comprises 5 wt % or less, such as 1 wt % or less of methanol.

Diluents may be included in the dimethyl ether. Examples of suitable diluents include nitrogen, argon and helium.

Suitably, the concentration of dimethyl ether may be in the range of from 0.1 mol % to 20 mol %, such as 1.5 mol % to 15 mol % based on the total gaseous feed to the process.

Preferably, dimethyl ether is utilised in the process in the vapour phase.

As water can inhibit the carbonylation of dimethyl ether to produce methyl acetate, the carbonylation process is preferably carried out under substantially anhydrous conditions. As used herein, "substantially anhydrous conditions" is taken to mean that the concentration of water is less than 1 mol %, preferably less than 0.5 mol %, more preferably less than 0.2 mol %, and most preferably less than 0.1 mol % based on the total gaseous feed to the process. Suitably, the dimethyl ether, carbon monoxide, hydrogen and the catalyst are dried prior to use in the process.

The carbon monoxide and hydrogen gases utilized in the present invention may be substantially pure, for example, carbon monoxide and hydrogen typically provided by suppliers of industrial gases, or they may contain low levels of impurities that do not interfere with the carbonylation reaction, such as methane and carbon dioxide.

Synthesis gas is a mixture of primarily carbon monoxide and hydrogen in varying amounts but it may also comprise small amounts of carbon dioxide and inert gases and is commercially available. Conventional processes for the production of synthesis gas include conversion reactions of hydrocarbon sources such as steam reforming and partial oxidation. Examples of hydrocarbon sources used in synthesis gas production include bio-mass, natural gas, methane, $C_2$-$C_5$ hydrocarbons, naphtha, coal and heavy petroleum oils.

Steam reforming generally comprises contacting a hydrocarbon with steam to form synthesis gas. The process may include the use of a catalyst, such as those based on nickel.

Partial oxidation generally comprises contacting a hydrocarbon with oxygen or an oxygen-containing gas such as air to form synthesis gas. Partial oxidation takes place with or without the use of a catalyst, such as those based on rhodium, platinum or palladium.

Suitably, in the present invention, a synthesis gas may be used as the source of carbon monoxide and hydrogen.

Optionally, the synthesis gas may also comprise one or more of carbon dioxide and inert gases.

The process may also be conducted in the presence of a diluent. Examples of suitable diluents include the inert gases, such as nitrogen, argon and helium.

On contact of the carbon monoxide and dimethyl ether with the catalyst under carbonylation reaction conditions, the carbonylation reaction is initiated and methyl acetate is produced as a reaction product. Hydrogen is largely unconsumed in the carbonylation process.

The present invention is conducted with a hydrogen to carbon monoxide molar ratio of at least 1, suitably in the range 1 to 10, for example 1 to 4, such as 1 to 2.

If desired, the process may be initially conducted under an excess of carbon monoxide. Thus, the process of the present invention may be initially conducted with a carbon monoxide to hydrogen molar ratio of at least 1 and thereafter carried out with a hydrogen to carbon monoxide molar ratio of at least 1.

In an embodiment of the present invention, the process may be initially carried out with a molar ratio of carbon monoxide to hydrogen in the range 1 to 15, such as in the range 1 to 4 and thereafter carried out with an hydrogen to carbon monoxide molar ratio in the range 1 to 10, for example 2 to 4, such as 1 to 2.

In a further embodiment the process may be initially carried out with a molar ratio of carbon monoxide to hydrogen of 4 and thereafter carried out with a hydrogen to carbon monoxide molar ratio in the range 1 to 2.

Suitably, the process may be initially carried out with a molar ratio of carbon monoxide to hydrogen in the range 1 to 15, such as in the range 1 to 4, and for example for a period of from about 10 minutes to about 500 hours, such as about 10 minutes to about 300 hours and thereafter the hydrogen partial pressure is increased such that the process is carried out with an hydrogen to carbon monoxide molar ratio of at least 1, for example in the range 1 to 2.

To improve catalytic selectivity, methyl acetate may be introduced into the process as an additional feed component. Suitably, methyl acetate may be introduced into the process in an amount of from 0.05 mol % to 5 mol %, such as from 0.5 mol % to 5 mol % based on the total gaseous feed to the process.

Suitably, the process is carried out at a temperature of from about 200° C. to about 350° C., for example of from about 280° C. to about 320° C.

The process may be carried out at a pressure of from about 1 to about 100 barg, such as of from about 10 to about 100 barg, for example of from about 20 to about 70 barg.

In an embodiment of the present invention, the process is carried out at a temperature of from about 280° C. to about 320° C. and at a pressure of from about 20 to about 70 bang.

Suitably, the process is carried out at a total gas hourly space velocity (GHSV) of from about 500 to about 40,000 h$^{-1}$, such as from about 2000 to about 10,000 h$^{-1}$.

Preferably, the process is carried out substantially in the absence of halides, such as iodide. By the term 'substantially' is meant that the total halide, for example, iodide content of the gaseous feeds to the process and the catalyst is less than 500 ppm, preferably less than 100 ppm.

If desired, the dimethyl ether, hydrogen and carbon monoxide may be contacted with a guard bed immediately before a bed of catalyst so as to remove impurities therefrom. Suitable guard beds include alumina.

Desirably, the process is carried out as a vapor phase process, for example as a fixed bed process. Where the process is operated as a vapor phase process the feedstock components prior to entering a reaction zone may be in the liquid phase. However, prior to contact with the catalyst, it may be desired to volatility liquid phase components, for example by use of a preheater.

The process may be carried out in a reaction zone by passing a gaseous feed of dimethyl ether, carbon monoxide and hydrogen, through one or more fixed beds of the catalyst maintained at the desired reaction temperature. It is, of course understood that a reaction zone may be one or more separate reactors with suitable means therebetween to assure that the desired reaction temperature is maintained at the entrance to each reactor.

Prior to use, the catalyst may be activated, for example by heating the catalyst to the desired reaction temperature, and over any desired period of time, under one or more of carbon monoxide, hydrogen and inert gases such as nitrogen and helium.

The reaction product of the process comprises methyl acetate. Typically the reaction product may further comprise additional components such as one or more of unreacted dimethyl ether, unreacted carbon monoxide and hydrogen.

Methyl acetate may be recovered from the process reaction product by any suitable means. Suitably, the reaction product is removed from a reaction zone in the form of a vapor, and thereafter condensed to a liquid fraction comprising the methyl acetate and a non-condensable gas fraction. The gas and liquid fractions may then be separated using known means such as knock-out drums or tangential inlet drums.

The methyl acetate recovered from the process reaction product may be sold as such or it may be utilized in downstream chemical processes. For instance, some or all of the recovered methyl acetate may be converted to acetic acid, for example by a hydrolysis process. Hydrolysis processes are known in the art, and include, for example reactive distillation in the presence of an acidic catalyst.

The process may be operated as a continuous or a batch process, preferably as a continuous process.

The invention is now illustrated with reference to the following non-limiting Examples.

EXAMPLES

Carbonylation Reaction Method

Carbonylation reactions were carried out in a pressure flow reactor unit consisting of 16 identical reactors of the type described in WO 2005063372. Each reactor had an internal diameter of 9.2 mm and was fitted with an internal tube of diameter 3.2 mm containing a 10 cm bed of corundum (particle size of 125-160 microns). On a dry mass basis (determined by loss on ignition of the composite measured by heating a catalyst to 600° C. at a ramp rate of about 30° C. per minute), about 2 g of a catalyst diluted with 3 ml of corundum (particle size 125 to 160 microns) was loaded into the reactor on top of the corundum. An 11 cm bed of corundum (particle size of 125-160 microns) was placed on top of the catalyst. A guard bed of 1 g gamma alumina of pellet size 125-160 microns was placed on top of the 11 cm corundum bed to a depth of about 2 cm.

The reactor was pressurized to a total pressure of 70 bar with a $1H_2:4CO$ gas feed at a flow rate of 12 l/h and then heated to a temperature of 280° C. and held at this temperature for 3 hours, after which the feed to the reactor was replaced by a carbonylation reaction feed of carbon monoxide, hydrogen and 2 mol % dimethyl ether at a total gas hourly space velocity of 4000 h$^{-1}$ and a molar ratio of $H_2:CO$ of 1:4. The reaction was continued under these conditions for six hours at which point the concentration of dimethyl ether was increased to 6 mol % and the reaction allowed to continue for a further 18 hours before the temperature was increased to 300° C. After 27 hours on stream, 0.5 mol % methyl acetate (MeOAc) was introduced into the carbonylation feed and the reaction allowed to continue for a further 332 hours at which point nitrogen was introduced into the feed to obtain a molar ratio of $H_2:CO:N_2$ of 1:2.5:1.5. After 459 hours on stream, the nitrogen feed was ceased and the molar ratio of $H_2:CO$ was changed to 1:1 and the reaction allowed to continue for a further 139 hours at which point the reaction was terminated. The exit stream from a reactor was passed periodically to a gas chromatograph to determine the concentration of reactants and carbonylation products.

Example 1

This Example illustrates the production of methyl acetate by the carbonylation of dimethyl ether in accordance with the Carbonylation Reaction Method described above using catalysts of 80 wt % $NH_4$-mordenite bound with 20 wt % alumina and having a silica:alumina molar ratio of 20. The catalysts were calcined for 1 hour in static air at temperatures of 400° C., 425° C., 475° C. and 500° C. and are referred to as Catalysts A to D respectively. The catalysts were employed in the carbonylation reaction in the form of 1.6 mm cylindrical extrudates.

Figure 1:
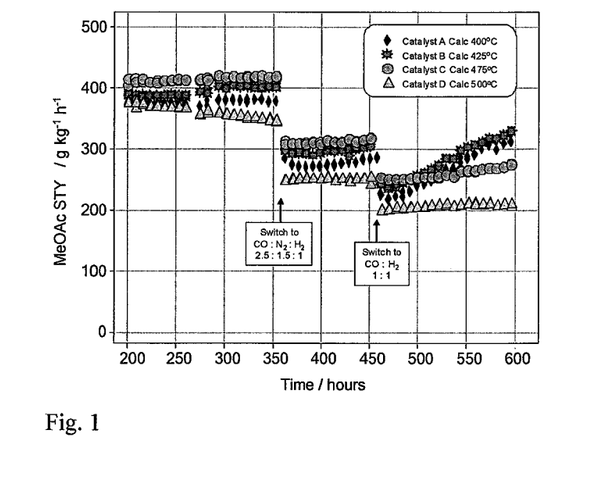
FIG. 1 depicts the space time yield to methyl acetate in grams per kilogram of catalyst per hour (STY MeOAc g kg$^{-1}$ h$^{-1}$) versus time on stream using Catalysts A to D calcined at 400° C., 425° C., 450° C. and 500° C. respectively.
Figure 2:
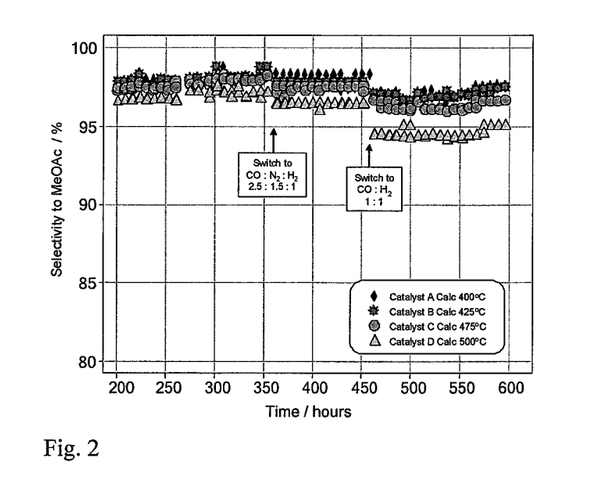
FIG. 2 depicts the selectivity (%) to methyl acetate versus time on stream using Catalysts A to D calcined at 400° C., 425° C., 450° C. and 500° C. respectively.

The space time yields (STY) to methyl acetate and selectivities of dimethyl ether to methyl acetate obtained after about 596 hours reaction time and at a $H_2$:CO molar ratio of 1:1 are shown in FIGS. 1 and 2 respectively.

FIG. 1 shows that after 350 hours reaction time, with a feed containing CO to $H_2$ at a molar ratio of 4:1, the most active catalyst for producing methyl acetate was Catalyst C calcined at 475° C., followed by Catalyst B calcined at 425° C., then Catalyst A calcined at 400° C., with Catalyst D calcined at 500° C. being significantly less active. On changing the CO to $H_2$ molar ratio from 4:1 to 1:1, Catalysts A and B calcined at 400° C. and 425° C., after the initial instantaneous reduction in activity due to the CO partial pressure decrease, showed a marked increase in activity with time on stream, such that at 598 hours reaction time these Catalysts were clearly the most active and were still increasing in activity at the end of the reaction. Catalyst C calcined at 475° C. also showed an increase in activity on switching to 1:1 CO:$H_2$, such that it was the third most active catalyst after 598 hours. Catalyst D calcined at 500° C. showed the least response to the change to 1:1 CO to $H_2$ and was the least active after 598 hours on stream. FIG. 2 shows that the selectivity to methyl acetate at the end of the reaction was materially lower for Catalyst D calcined at 500° C. than for the Catalysts A to C calcined at low temperature.

Thus, as can clearly be seen from FIGS. 1 and 2, the low temperature calcined Catalysts A to C provide materially enhanced catalytic performance than the high temperature calcined catalyst, Catalyst D.

Example 2

A catalyst of 80 wt % ammonium mordenite bound with 20 wt % alumina and a silica:alumina molar ratio of 20 was calcined for 2.5 hours at a temperature of 400° C. This catalyst referred to as Catalyst E was used to carbonylate dimethyl ether with carbon monoxide in the presence of hydrogen in accordance with the above-described Carbonylation Reaction Method using the carbonylation reaction feeds and reaction conditions given in Table 1 below. Nitrogen was not introduced into the carbonylation reaction feed in this Example.

TABLE 1

| Time (hours) | $H_2$:CO | DME (mol %) | MeOAc (mol %) | Temperature (° C.) |
|---|---|---|---|---|
| 0-2 | 1:4 | 2 | 0 | 280 |
| 2-18 | 1:4 | 10 | 0 | 280 |

TABLE 1-continued

| Time (hours) | $H_2$:CO | DME (mol %) | MeOAc (mol %) | Temperature (° C.) |
|---|---|---|---|---|
| 18-21 | 1:4 | 10 | 0 | 300 |
| 21-162 | 1:4 | 10 | 0.5 | 300 |
| 162-163 | 1:4 | 0 | 0 | 300 |
| 163-169 | 2:1 | 0 | 0 | 300 |
| 169-410 | 2:1 | 10 | 0.5 | 300 |
| 410-500 | 2:1 | 10 | 0.5 | 320 |

Figure 3:
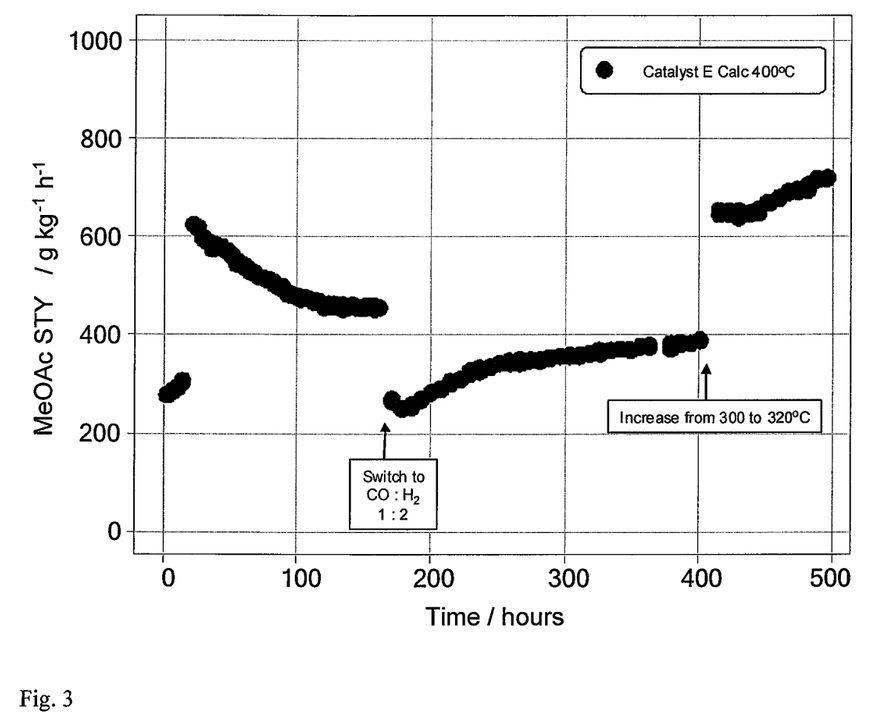
FIG. 3 depicts the space time yield to methyl acetate in grams per kilogram of catalyst per hour (STY MeOAc g kg$^{-1}$ h$^{-1}$) versus time on stream using Catalyst E calcined at 400° C.

The space time yields to methyl acetate are shown in FIG. 3. As can be seen from FIG. 3, on switching the $H_2$:CO molar ratio from 1:4 to 2:1 Catalyst E calcined at 400° C., after the initial instantaneous reduction in activity due to a decrease in CO partial pressure, showed a marked increase in activity with time on stream, such that at 410 hours reaction time it had regained most of its carbonylation activity despite the reduced CO partial pressure.

Example 3

This Example illustrates the production of methyl acetate by the carbonylation of dimethyl ether in the presence of hydrogen and catalysts calcined at 400° C., 450° C., 500° C. and 550° C.

Catalysts F to I were prepared by calcining samples of ammonium mordenite (silica:alumina molar ratio of 20) at calcination temperatures of 400° C., 450° C., 500° C. and 550° C. respectively, using the following procedure. A catalyst sample was placed in a muffle oven under a static atmosphere of air and subjected to the following temperature programme. The temperature was increased from room temperature to 90° C. at a ramp rate of 3° C./min and held at that temperature for 2 hours. The temperature was then increased from 90° C. to 110° C. at a ramp rate of 1° C./min and held at that temperature for 2 hours. The temperature was then increased from 110° C. to the desired calcination temperature (Catalyst F, time to reach 400° C. was 60 minutes; Catalyst G, time to reach 450° C. was 70 minutes; Catalyst H, time to reach 500° C. was 80 minutes; Catalyst I, time to reach 550° C. was 90 minutes) and held at the calcining temperature for a period of 3 hours before being allowed to cool to 90° C. The catalyst was then removed from the oven and allowed to cool to room temperature.

Each of Catalysts F to I was pressed, crushed and sieved to particle size 125 to 160 microns and 1.95 g of each catalyst was diluted with 3 ml of gamma alumina (SAS 200 gamma alumina ex BASF, particle size 125 to 160 microns) and employed in the carbonylation of dimethyl ether with carbon monoxide in the presence of hydrogen in accordance with the above-described Carbonylation Reaction Method using the carbonylation reaction feed and reaction conditions given in Table 2 below. In this Example 3, nitrogen was not introduced during the carbonylation reaction.

TABLE 2

| Time (hours) | $H_2$:CO | DME (mol %) | MeOAc (mol %) | Temperature (° C.) |
|---|---|---|---|---|
| 0-6 | 1:4 | 2 | 0 | 280 |
| 6-24 | 1:4 | 6 | 0 | 280 |
| 24-26 | 1:4 | 6 | 0 | 300 |
| 26-390 | 1:4 | 6 | 0.5 | 300 |
| 390-509 | 1:1 | 6 | 0.5 | 300 |
| 509-647 | 1:1 | 6 | 0.5 | 310 |

The space time yields (STY) to methyl acetate after about 378 hours and 500 hours reaction time and at $H_2$:CO molar ratios of 1:4 and 1:1 respectively and a reaction temperature of 300° C. are shown in Table 3 below.

TABLE 3

| Catalyst | Calcining Temperature (° C.) | STY at 1:4 $H_2$:CO (g · kg$^{-1}$h$^{-1}$) | STY at 1:1 $H_2$:CO (g. kg$^{-1}$h$^{-1}$) |
|---|---|---|---|
| F | 400 | 351 | 355 |
| G | 450 | 344 | 319 |
| H | 500 | 300 | 257 |
| I | 550 | 186 | 160 |

As can be seen from Table 3, in response to changing from conditions of excess carbon monoxide to reduced carbon monoxide partial pressure (by increasing the hydrogen to carbon monoxide molar ratio), the low temperature calcined Catalysts F and G clearly perform significantly better than Catalysts H and I calcined at higher temperature.

The space time yields (STY) to methyl acetate after 646 hours reaction time and at a $H_2$:CO molar ratio of 1:1 and a reaction temperature of 310° C. are shown in Table 4 below.

TABLE 4

| Catalyst | Calcining Temperature (° C.) | STY (g · kg$^{-1}$h$^{-1}$) |
|---|---|---|
| F | 400 | 662 |
| G | 450 | 669 |
| H | 500 | 517 |
| I | 550 | 309 |

As can be seen from Table 4, after about 256 hours in the presence of an equimolar amount of hydrogen, the low temperature calcined Catalysts F and G significantly outperform Catalysts H and I which were subjected to calcination at higher temperatures.

Example 4

Catalysts J to M were prepared by calcining samples of H-mordenite bound with 20% alumina at temperatures of 350° C., 400° C., 450° C. and 500° C. respectively. Catalysts J to M were used to carbonylate dimethyl ether with carbon monoxide in the presence of hydrogen in accordance with the above-described Carbonylation Reaction Method and employing the carbonylation reaction feeds and reaction conditions as given in Table 5 below.

TABLE 5

| Time (hours) | $H_2$:CO | DME (mol %) | MeOAc (mol %) | Temperature (° C.) |
|---|---|---|---|---|
| 0-6 | 1:4 | 2 | 0 | 280 |
| 6-24 | 1:4 | 6 | 0 | 280 |
| 24-27 | 1:4 | 6 | 0 | 300 |
| 27-310 | 1:4 | 6 | 0.5 | 300 |
| 310-450 | 1:1 | 6 | 0.5 | 300 |

Figure 4:
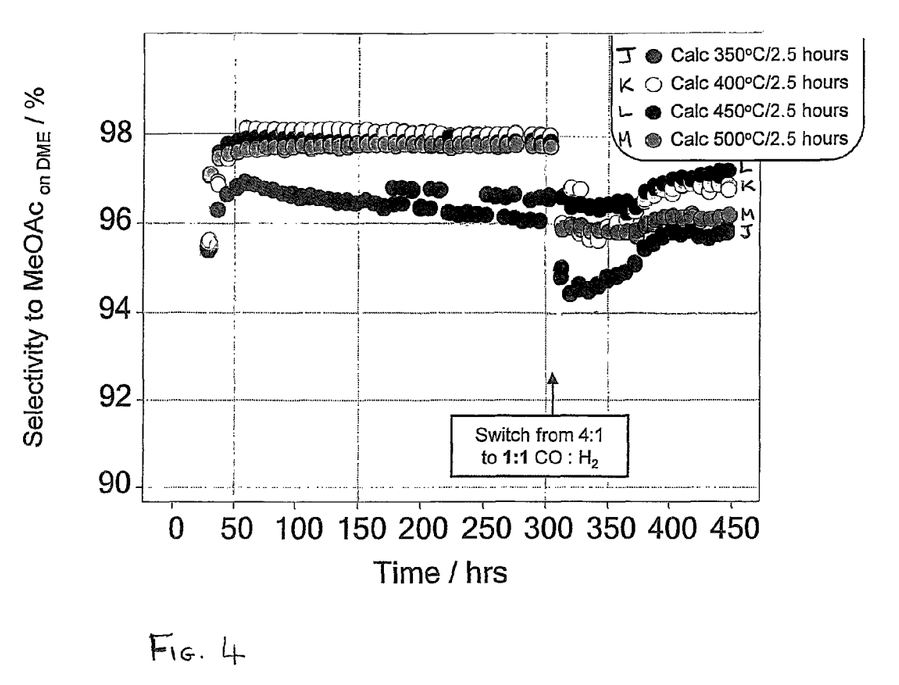
FIG. 4 depicts the selectivity (%) to methyl acetate versus time on stream using Catalysts J to M calcined at 350° C., 400° C., 450° C. and 500° C. respectively.

The selectivities of dimethyl ether to methyl acetate obtained after about 450 hours reaction time are shown in FIG. 4. As can be seen from FIG. 4 the catalysts calcined at 400° C. and 450° C. are the most selective at a $H_2$ to CO molar ratio of 1:1. The catalysts calcined at 350° C. and 500° C. provide poor selectivity at a $H_2$ to CO molar ratio of 1:1.

The invention claimed is:

1. A process for the production of methyl acetate which comprises carbonylating dimethyl ether with carbon monoxide in the presence of hydrogen and a zeolite catalyst wherein the process is carried out with a molar ratio of hydrogen to carbon monoxide of at least 1 and the catalyst has been calcined at a temperature of from about 375° C. to about 475° C.

2. A process for improving the performance of a zeolite catalyst in the production of methyl acetate by the carbonylation of dimethyl ether with carbon monoxide in the presence of hydrogen wherein the process is carried out with a molar ratio of hydrogen to carbon monoxide of at least 1 and the catalyst has been calcined at a temperature of from about 375° C. to about 475° C.

3. A process according to claim 1 wherein the process is initially conducted with a carbon monoxide to hydrogen molar ratio of at least 1 and thereafter carried out with an hydrogen to carbon monoxide molar ratio of at least 1.

4. A process according to claim 3 wherein the process is initially conducted with a carbon monoxide to hydrogen molar ratio in the range 1 to 4:1 and thereafter carried out with an hydrogen to carbon monoxide molar ratio in the range 1 to 2:1.

5. A process according to claim 1 wherein the catalyst is calcined at a temperature of from about 400° C. to about 475° C.

6. A process according to claim 5 wherein the catalyst is calcined at a temperature of from about 400° C. to about 450° C.

7. A process according to claim 1 wherein the catalyst is calcined in an inert atmosphere or in an oxidising atmosphere.

8. A process according to claim 7 wherein the oxidising atmosphere is air.

9. A process according to claim 1 wherein the catalyst is calcined for a duration of from about 10 minutes to about 10 hours.

10. A process according to claim 9 wherein the catalyst is calcined for a duration of from about 1 hour to about 3 hours.

11. A process according to claim 1 wherein the molar ratio of hydrogen to carbon monoxide is in the range 1 to 10:1.

12. A process according to claim 11 wherein the molar ratio of hydrogen to carbon monoxide is 1 to 2:1.

13. A process according to claim 1 wherein the zeolite contains at least one channel or pocket which is defined by an 8-member ring and the 8-member ring channel or pocket is interconnected with at least one channel defined by a ring with 10 or 12 members.

14. A process according to claim 13 wherein the zeolite is selected from zeolites of framework type MOR, FER, OFF, CHA, GME and MFS.

15. A process according to claim 13 wherein the zeolite is selected from mordenite, ferrierite and offretite.

16. A process according to claim 15 wherein the zeolite is a mordenite in a hydrogen-exchanged or an ammonium-exchanged form.

17. A process according to claim 1 wherein the zeolite is combined with a binder.

18. A process according to claim 17 wherein the binder is a refractory inorganic oxide binder.

19. A process according to claim 18 wherein the refractory inorganic oxide binder is selected from aluminas, silica-aluminas or silicas.

20. A process according to claim 17 wherein the binder is present in an amount of 10% to 30% by weight.

21. A process according to claim 17 wherein the zeolite combined with the binder is in the form of an extrudate.

22. A process according to claim 1 wherein the process is carried out at a concentration of water of less than 1 mol % based on the total gaseous feed to the process.

23. A process according to claim 1 wherein synthesis gas is used as the source of carbon monoxide and hydrogen.

24. A process according to claim 1 wherein the process is carried out at a temperature in the range 200° C. to 350° C.

25. A process according to claim 24 wherein the process is carried out at a temperature in the range 280° C. to 320° C.

26. A process according to claim 1 wherein the process is carried out at a total pressure of from 10 to 100 barg.

27. A process according to claim 1 wherein methyl acetate is introduced into the process in an amount of from 0.05 mol % to 5 mol % based on the total feed to the process.

28. A process according to claim 1 wherein the process is carried out as a vapour phase process.

29. A process according to claim 1 wherein methyl acetate is recovered from the process and some or all of the recovered methyl acetate is converted to acetic acid.

* * * * *